Patented Apr. 4, 1939

Plant Pat. 325

UNITED STATES PATENT OFFICE

325

PEACH TREE

John Ugene Nametz, Benton Harbor, Mich., assignor to Greening Nursery Company, Monroe, Mich.

No Drawing. Application November 15, 1938, Serial No. 240,557

1 Claim. (Cl. 47—62)

My new discovery relates to improvements in the variety known as Halehaven and is in every respect identical with Halehaven except that the new variety ripens one week to ten days earlier.

This new variety occurred several years ago as a limb sport on a Halehaven tree in my orchard near Benton Harbor, Michigan. Upon discovery of the limb sport I top-grafted a Saunders peach tree with buds of the sport. Limbs developed from these bud grafts have reproduced fruit which has the same early-ripening quality possessed by the original limb sport.

Any standard description of the Halehaven peach would describe this new variety in all respects except the ripening date. However, the chief characteristics of the plant and fruit of this new variety are set forth below:

Tree:

Semi-spreading; vigorous; very hardy; prolific and early bearer.

Fruit:

*Size.*—Large—weight 5½ to 6 ounces. Uniform in size.

*Shape.*—Globose.

*Cavity.*—Deep and abrupt.

*Suture.*—Shallow.

*Apex.*—Sharp-pointed but depressed.

*Skin.*—Moderately tough; very highly colored even while still firm, enabling it to be picked early enough to be a good shipper.

*Flesh.*—Rich, golden yellow and of excellent quality.

*Pit.*—Small and entirely free.

Ripening:

Even and highly colored.

Shipping quality:

Excellent.

Having thus disclosed my discovery, I claim:

A new variety of peach tree producing peaches identical with those of the variety Halehaven but with a ripening season one week to ten days earlier than that of Halehaven.

JOHN UGENE NAMETZ.